United States Patent [19]

Dhaon et al.

[11] Patent Number: 5,753,621
[45] Date of Patent: May 19, 1998

[54] PULMONARY SURFACTANT PROTEIN FRAGMENTS

[75] Inventors: Madhup Krishna Dhaon, Mundelein; Edwin Orville Lundell; Virender Kumar Sarin, both of Libertyville, all of Ill.; Constance Hope Baxter, Galena; Darryl Robin Absolom, Columbus, both of Ohio

[73] Assignee: Abbott Laboratories, Abbott Park, Ill.

[21] Appl. No.: 435,019

[22] Filed: May 4, 1995

Related U.S. Application Data

[62] Division of Ser. No. 296,898, Aug. 29, 1994, Pat. No. 5,547,937, which is a division of Ser. No. 866,916, Apr. 10, 1992, abandoned.

[51] Int. Cl.$^6$ .............. A61K 38/00; C07K 7/10; C07K 7/08
[52] U.S. Cl. ................. 514/12; 514/13; 514/14; 514/15; 530/324; 530/326; 530/327; 530/328
[58] Field of Search .............. 530/324, 326–328; 514/12, 13, 15

[56] References Cited

U.S. PATENT DOCUMENTS

| | | | |
|---|---|---|---|
| 4,234,475 | 11/1980 | Sokol | 530/350 |
| 4,861,756 | 8/1989 | Jackson | 514/11 |
| 5,055,553 | 10/1991 | Jacobs et al. | 530/300 |
| 5,164,369 | 11/1992 | Cochrane et al. | 514/12 |
| 5,238,920 | 8/1993 | Sarin et al. | 514/12 |
| 5,510,333 | 4/1996 | Angelastro et al. | 514/18 |

FOREIGN PATENT DOCUMENTS

| | | |
|---|---|---|
| 0 307 513 | 12/1987 | European Pat. Off. . |
| 0 413 957 | 7/1990 | European Pat. Off. . |

OTHER PUBLICATIONS

"Surfactant Chemical Composition and Biophysical Activity in Acute Respiratory Distress Syndrome", Gregory et al., *The American Society for Clinical Investigation, Inc.*, vol. 88, pp. 1976–1981.

"Enzymic Inactivation of Oxytocin. III. Desthiooxytocin And S,S'-Debenzyldihydrooxytocin as Oxytocinase Inhibitors and Substrates", Berankova et al. *Czechoslovak Academy of Science*, vol. 26, pp. 2557–2561, 1961.

"Conformation of Biopolymers", Ramachandran, *Academic Press Inc. (London) Ltd.*, vol. 1, pp. 215–216, 1967.

"The Role of Sulfur in Proteins", Liu, *The Proteins*, vol. III, pp. 239 and 255, 1977.

Preparation of S,S'–Dibenzyloxytocin and Its Reconversion to Oxytocin. Gordon, et al. *P.S.E.B.M.*, V. 84, 1953.

"cDNA and deduced amino acid sequence of human pulmonary surfactant–associated proteolipid SPL(Phe)", Glasser et al. *Biochemistry*, vol. 84, 1987, pp. 4007–4011.

"Interactions with Peptide Paradigms for the Sufactant Protein SP–B+", Vincent et al. *Biochemistry*, 1991 30, 8395–8401.

"Human surfactant polypeptide SP–B Disulfide bridges, C–terminal end, and peptide analysis of the airway form", Johansson et al. *Elsevier Science Puclishers B.V.*, vol. 301, No. 2, 165–167, 1992.

"Exogenous Surfactant for Human Lung Disease", Taeusch, et al. *American Rev.Respiratory Diseases*, vol. 128, 791–794, 1983.

"Biophysical and biological activity of a synthetic 8.7 kDa hydrophobic pulmonary surfactant protein SP–B", *Proc. National Acad. Science*, vol. 87, pp. 2633–2637, 1990.

"Pulmonary Surfactant Therapy", *The New England Journal of Medicine*, Drug Therapy–Jobe, vol. 328, No. 12, pp. 861–868.

*Primary Examiner*—Douglas W. Robinson
*Assistant Examiner*—S. G. Marshall
*Attorney, Agent, or Firm*—Lonnie Drayer; Donald O. Nickey; Thomas D. Brainard

[57] ABSTRACT

This invention discloses that certain fragments of a pulmonary surfactant protein exhibit unexpected surface activity. These protein fragments are useful in preparing formulations for the treatment of respiratory distress syndrome.

23 Claims, No Drawings

PULMONARY SURFACTANT PROTEIN FRAGMENTS

This is a Divisional of application Ser. No 08/296,898 filed on Aug. 29, 1994, now U.S. Pat. No. 5,547,937, which is a Divisional of application Ser. No. 07/866,916 filed Apr. 10, 1992, now abandoned.

TECHNICAL FIELD

This invention relates to novel polypeptides and the use of these peptides in the preparation of formulations for the treatment of respiratory disease.

BACKGROUND OF THE INVENTION

The present invention relates to novel compositions of matter and methods for the treatment of respiratory distress with these novel compositions. This invention also relates to the use of polypeptides (protein fragments) which enhance the surfactant-like properties of phospholipids. More specifically, the present invention relates to novel polypeptides comprising fragment replicas and analogs of fragment replicas of the naturally occurring low molecular weight hydrophobic surfactant associated protein known as SP-B and to their use in the formulation of novel medicaments useful in the establishment, modification and/or maintenance of pulmonary surface tension.

Specifically incorporated herein, by reference for purposes of establishing the background of the present invention, are the teachings and disclosures of the following U.S. patent applications:
1. U.S. patent application Ser. No. 860,239, filed May 6, 1986;
2. U.S. patent application Ser. No. 060,719, filed Jun. 10, 1987;
3. U.S. patent application Ser. No. 101,680, filed Oct. 1, 1987;
4. U.S. patent application Ser. No. 175,741, filed Mar. 31, 1988;
5. U.S. patent application Ser. No. 897,183, filed Aug. 15, 1986;
6. U.S. patent application Ser. No. 397,151, filed Aug. 22, 1989.

Also incorporated herein by reference is U.S. Pat. No. 4,659,805 which discloses and claims a high molecular weight surfactant protein known as SP-A.

These references disclose the discovery, method of isolation, characterization and use of a family of naturally occurring mammalian surfactant-associated proteins. Members of this family have been designated as SP-A, SP-B and SP-C. These proteins are known to have the capacity to affect the surfactant-like activity of both natural and synthetic phospholipids. It should be noted that the associated scientific literature also uses the nomenclature of SAP-B, SAP-(Phe), SAP-6 (Phe), and SPL-(Phe) for SP-B. SP-C is also referred to as SAP-C, SAP-(Val), SAP-6 (Val) and SPL (Val) in the prior art. These two proteins (SP-B and SP-C) are distinct gene products with unique amino acid sequences. Both proteins are derived from proteolytic processing of larger precursor proteins synthesized by pulmonary type II epithelial cells.

SP-B is generated by cleavage of the precursor protein at a glutamine-phenylalanine peptide bond resulting in the naturally occurring protein having 78 amino acid residues, with an N-terminal residue of phenylalanine and a simple molecular weight of about 8,700. SP-B isolated from human lung migrates on polyacrylamide gels as an entity having a relative molecular weight (Mr) of 7–8,000 after sulfhydryl reduction. Without sulfhydryl reduction the naturally occurring protein is also found as large oligiomers. SP-B is extremely hydrophobic, a physical property which is consistent with its in vivo strong association with phospholipids and solubility in organic solvents such as chloroform and methanol.

Also incorporated herein by reference is U.S. Ser. No. 351,157 which discloses and claims that the amino and carboxyl terminal ends of the SP-B protein can be generated by means of solid phase peptide synthesis and yield, in combination with certain carrier lipids, admixtures which exhibit substantial surface activity. Also incorporated herein by reference is the article published by C. G. Cochrane and S. D. Revak in the journal SCIENCE 254 566–568, 1991 (Oct. 25, 1991). This article describes the surface active properties of SP-B-like synthetic peptide analogs whose sequence is derived from an attempt to emulate the hydropathy profile (hydrophobic/hydrophilic domain mapping) of full length native SP-B. As such the peptides evaluated have an amino acid sequence which does not resemble the sequence found in the native SP-B molecule. The present application differs from the SCIENCE article in that the synthetic peptides described herein are based strictly on the amino acid sequence found in the carboxyl terminal region of native SP-B protein.

SP-C has an amino terminal glycine residue, a molecular weight of about 3,700, a polyvaline sequence, and, like SP-B, is also extremely hydrophobic. In addition, both proteins (SP-B and SP-C) are substantially resistant to enzyme degradation by proteases (trypsin, chymotrypsin and staphylococcus nucleotide V-8), endoglycosidase F, and collagenase. Neither SP-B nor SP-C exhibits any degradation or alteration in their molecular weight distribution following treatment with these enzymes. In this behavior, as well as on the basis of amino acid sequence information, the proteins are clearly different from the more hydrophilic and higher molecular weight protein SP-A (also known as SAP-35).

SP-A is present in natural lung surfactant material and has a reduced molecular weight of 30–36,000. SP-A is a glycoprotein containing an internal collagen-like region which is rich in glycine and hydroxyproline. This protein has a N-linked complex carbohydrate and a calcium binding site in the C-terminal globular domain. SP-A is known to bind to phospholipids and is thought to confer important structural organization to the surfactant lipids. This protein is also believed to play a role in preventing the inhibition of pulmonary surfactant activity by plasma or other proteins.

The complete amino acid sequence of SP-B and SP-C has been determined from amino acid analysis and deduced from cDNA's derived from the mRNA's encoding the proteins. The SP-B and SP-C proteins are available as isolates from natural sources, such as bronchioalveolar lung washes and minced lung tissue or as products resulting from the application of recombinant DNA methodologies. When formulated with phospholipids (including synthetic phospholipids) these proteins provide compositions useful in the treatment of pulmonary disorders.

As is often the case with biologically active substances, the isolation of substantial quantities of hydrophobic SP-B and SP-C proteins from natural sources is expensive and labor intensive. Likewise, production of these proteins by recombinant DNA techniques requires substantial effort in terms of design and achieving optimal host/vector expression systems to facilitate production of the proteins. In addition, considerable effort is required to develop effective isolation strategies to separate and purify the expressed protein of interest from the unwanted material. With respect to the specific case of SP-B, the low molecular weight, extreme hydrophobicity and large number of cysteine residues markedly complicates commercial development of efficient expression and/or isolation procedures.

Due to these problems, commercial production of SP-B via isolation from natural materials or expression of the protein via recombinant DNA strategies is difficult. The medical community has a need for commercial quantities of SP-B and the present invention fulfills that need through the discovery that only a small portion of the SP-B protein molecule is required for the formulation of an effective pulmonary surfactant.

The usefulness of the naturally occurring SP-B and SP-C proteins resides in their ability to improve significantly the surface tension lowering capacity and respreadability of phospholipid admixtures. Natural SP-B and SP- C have been shown, both individually as well as in combination, to facilitate this improvement in surfactant-like activity of phospholipids. However, what has not previously been established is whether the entire protein sequence is necessary to achieve this optimum condition or whether only certain regions or fragments of these proteins, either alone or in certain combinations, might achieve the same result. The prior art fails to suggest, disclose or contemplate the instant discovery. Further one skilled in the art can not a priori determine what fragments will evidence utility or that certain fragments will have activity comparable to or exceeding that of the complete natural protein.

It is clear that synthesis of replica fragments, or analogs thereof, would provide numerous advantages over the chemical or recombinant synthesis of the entire sequence. These advantages include cost, ease of production, isolation and purification.

DISCLOSURE OF THE INVENTION

There is disclosed a composition of matter which comprises at least one fragment of the SP-B protein which exhibits surfactant activity when admixed with phospholipids, said fragment being that portion of the SP-B protein which contains at least a portion of the carboxyl terminal amino acid sequence and substitution, deletion and addition analogs thereof.

There is also disclosed a composition of matter comprising said SP-B fragments or analogs thereof in combination with at least one lipid. The lipid is selected from the group consisting of synthetic phospholipids, naturally occurring phospholipids, neutral lipids, cholesterol, cholesteryl esters, phosphatidylcholine, disaturatedphosphatidylycholine, phosphatidylglycerol, dipalmitoyl phosphatidylcholine, phosphatidylinisotyl and mixtures thereof.

The most preferred lipids are a mixture comprising dipalmitoyl-sn-phosphatidylcholine (DPPC), egg phosphatidylglycerol (PG) and palmitic acid (PA). Also disclosed is a method for the treatment of pulmonary surfactant deficient states (e.g. hyaline membrane disease) and/or abnormal surfactant states (e.g. acute respiratory distress syndrome), said method comprising administration of an effective amount of a surfactant composition to a patient in need of treatment, said surfactant composition consists of at least one SP- B fragment, said fragment contains at least a terminal amino acid sequence; and at least one lipid.

According to the present invention, novel, non-naturally occurring synthetic peptides are disclosed which have the ability to enhance markedly the surfactant-like activity of natural and/or synthetic phospholipids. The synthetic polypeptides of this invention comprise replicas of portions (fragments) of the known continuous amino acid sequences of naturally occurring SP-B, which may be combined with phospholipids alone, or combined with of two or more SP-B analog replicas, and/or combinations of one or more SP-B analog replicas with natural, synthetic or recombinant SP-C and/or SP-A. The polypeptide fragments of the invention are readily and economically synthesized via chemical or recombinant technologies and may be formulated with natural or synthetic phospholipids to yield admixtures which exhibit markedly enhanced surfactant-like activity as compared to the phospholipid mixtures alone.

Best Mode for Carrying Out the Invention

A number of polypeptides of various lengths and corresponding to various regions contained within the carboxyl terminal portion of the natural SP-B protein (as described previously in U.S. Ser. No. 397,151) were synthesized by means of solid phase peptide synthesis. However, identical and/or similar fragments could also be produced by known recombinant DNA methods. This invention contemplates that the various SP-B fragments can be produced using recombinant technologies and that one skilled in the art of recombinant synthesis will appreciate that fragments of certain size (length of amino acid sequence) will be more readily produced via this technology. Thus, the scope of this invention is intended to include all SP-B fragments that contain a terminal amino acid sequence which exhibit surfactant activity and which can be facilely produced using either peptide synthesis or recombinant technologies.

Table 1 sets forth the molecular mass, position, and number of amino acids constituting the various synthesized SP-B fragments and the associated nomenclature for the purposes of this application.

TABLE 1

Description of the Nomenclature, Molecular Mass, Position and Number of Amino Acid Residues of Synthesized SP-B Peptide Fragments.

| Nomenclature | Molecular Mass | Position | # of Amino Acids |
|---|---|---|---|
| SP-B(53–70) | 2044 | 53–70 | 18 |
| SP-B(53–78) | 2977 | 53–78 | 26 |
| SP-B(53–78)diAcm | 3119 | 53–78 | 26 |
| SP-B(58–70) | 1469 | 58–70 | 13 |
| SP-B(58–78)diAla | 2336 | 58–78 | 21 |
| SP-B(58–78)diAcm | 2541 | 58–78 | 21 |
| SP-B(63–70) | 913 | 63–70 | 8 |
| SP-B(63–78)diAla | 1780 | 63–78 | 16 |
| SP-B(63–78)diAcm | 1985 | 63–78 | 16 |
| SP-B(66–78) | 1498 | 66–78 | 13 |
| SP-B(66–78)diLys | 1552 | 66–78 | 13 |
| SP-B(66–78)diAla | 1436 | 66–78 | 13 |
| SP-B(66–78)diAcm | 1641 | 66–78 | 13 |
| SP-B(69–78) | 1160 | 69–78 | 10 |
| SP-B(69–78)diAla | 1098 | 69–78 | 10 |
| SP-B(69–78)diAcm | 1302 | 69–78 | 10 |

As the result of formulation experiments and testing (as hereinafter described) the inventors have determined that certain of these fragments exhibit the unexpected, unpredicted, unusual and surprising ability to facilitate enhanced surface activity of phospholipid admixtures.

It is contemplated that the polypeptides of this invention may comprise addition analogs (wherein one or more amino acid residues which are not naturally present in a given SP-B sequence are provided in the synthetic polypeptide at terminal or intermediate locations), deletion analogs (wherein one or more residues are deleted from a natural sequence), substitution analogs (wherein one or more residues are replaced by other amino acid residues) and replicate analogs (wherein one or more residues are repeated, replicated, in a natural sequence). Specifically comprehended are interspecies hybrid analogs comprising composite replicas of more than one species (i.e. human, canine, bovine, porcine, etc.) of naturally occurring SP- B proteins and those analogs wherein D-forms of amino acids replace the naturally occurring L-forms. The polypeptides of this invention preferably retain the overall hydrophobic character of the SP-B protein are expected also to retain substantial elements of secondary and tertiary conformation.

SP-B(66-78)diAla;

SP-B(66-78)diLys;

SP-B(69-78)diAla.

In each of these analogs, the two cysteine residues (located at positions 71 and 77) were replaced with either alanine or lysine. Such analogs would also obviate the possibility of inter- and intra-molecular polymerization since disulphide linkage is no longer possible in the absence of the cysteines.

The most preferred polypeptides of the invention include:

(a) SP-B (53-78) diAcm having the amino acid sequence:

```
                                                          Acm            Acm
                                                           |              |
NH2—Y—S—V—I—L—L—D—T—L—T—L—G—R—M—L—P—P—Q—V—C—R—L—V—L—R—C—S—OH
    |                                                                    |
    53                                                                   78
```

(b) SP-B (58-78)diAcm having the amino acid sequence:

```
                                          Acm            Acm
                                           |              |
NH2—L—D—T—L—L—G—R—M—L—P—Q—L—V—C—R—L—V—L—R—C—S—OH
    |                                                    |
    58                                                   78
```

By way of example of the above, the following peptide analogs were synthesized and demonstrated to exhibit utility in that they were shown to lower substantially the measured minimum surface tension value of lipid admixtures into which these peptides were incorporated:

which is seen to constitute a replica of the final, 21 carboxyl terminal, amino acid residues of the SP-B protein but in which the oxidative capacity of the two cysteine residues (located at amino acid sequence positions 71 and 77 respectively) is blocked through the covalent attachment of the two Acm groups;

(c) SP-B (58-78) diAla having the amino acid sequence:

```
NH2—L—D—T—L—L—G—R—M—L—P—Q—L—V—A—R—L—V—L—R—A—S—OH
    |                                                |
    58                                               78
```

SP-B(53-78)diAcm;
SP-B(58-78)diAcm;
SP-B(63-78)diAcm;
SP-B(66-78)diAcm;
SP-B(69-78)diAcm.

In each of these cases the identified peptide sequence, which corresponds to a portion of the native SP-B amino which is seen to constitute a replica of the final, 21 carboxyl terminal, amino acid residues of the SP-B protein but in which the oxidative capacity of the two cysteine residues is obviated through the substitution of two alanine residues in place of the two cysteines located at amino acid sequence positions 71 and 77 respectively.

(d) SP-B(63-78)diAla having the amino acid sequence:

```
NH2—G—R—M—L—P—Q—L—V—A—R—L—V—L—R—A—S—OH
    |                                    |
    63                                   78
``` acid sequence, has been modified through the covalent attachment to each of the two cysteine residues, located at amino acid positions 71 and 77 respectively, an S-acetamidomethyl (Acm) group. (The Acm group is useful in that it will prevent intra- and/or inter-molecular polymerization through oxidation and subsequent disulphide linkage).

In addition, by way of example, the following substitution analogs were also prepared:

SP-B(58-78)diAla;

SP-B(63-78)diAla;

which is seen to constitute a replica of the final, 16 carboxyl terminal, amino acid residues of the SP-B protein but in which the oxidative capacity of the two cysteine residues is obviated through the substitution of two alanine residues in place of the two cysteines located at amino acid sequence positions 71 and 77 respectively.

(e) SP-B(66-78)diAla having the amino acid sequence:

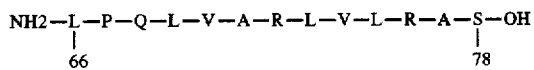

which is seen to constitute a replica of the final, 13 carboxyl terminal, amino acid residues of the SP-B protein but in which the oxidative capacity of the two cysteine residues is obviated through the substitution of two alanine residues in place of the two cysteines located at amino acid sequence positions 71 and 77 respectively.

As with native SP-B, (complete protein) the polypeptides of this invention are readily formulated with either natural or synthetic phospholipids to yield admixtures which are useful in the treatment of pulmonary surfactant deficient (eg. hyaline membrane disease) and/or abnormal (eg. acute respiratory distress syndrome, A-RDS) surfactant states, and for pulmonary drug delivery systems.

Other aspects and advantages of the invention will be apparent upon consideration of the following detailed description of the illustrative embodiments hereof.

EXPERIMENTAL

The following examples relate to the synthesis and testing of polypeptides of the invention. More specifically, Examples 1-3 relate to the synthesis of polypeptides patterned on the entire amino acid sequence for the human SP-B protein. Table 1 (supra) sets forth the position, molecular weight and number of amino acids constituting the various synthesized SP-B fragments. All fragments were synthesized, cleaved and purified. Examples 4 and 5 relate to the formulation and testing of polypeptide/phospholipid admixtures. The data illustrate markedly improved surfactant-like activity of the carrier phospholipids when combined with the peptides of this invention.

The peptides described in this invention were prepared by adaptation of conventional methods in solid phase peptide synthesis (SPPS) as described in "Solid Phase Peptide Synthesis" by J. M. Stewart and J. D. Young, 2nd Edition (1984). The compounds of the invention may also be prepared by partial solid phase synthesis, fragment condensation methods and classical solution methods as exemplified by the methods described in "peptide synthesis", second edition, M. Bodansky, Y. S. Klausner and M. A. Ondetti (1976).

General Procedure

In SPPS, the C-terminal amino residue of the peptide was anchored to a polystyrene support via an ester linkage. The peptide chain was elongated by a series of coupling reactions in which the constituent amino acids were added in the desired sequence. The N-x-protecting group for the various amino acids was t-butyloxycarbonyl (Boc), the coupling reagent was diisopropylcarbodiimide (DIC), the activating agent was 1-hydroxybenzotriazole (HOBt) in a suitable solvent such as dichloromethane (DCM) or dimethylformamide (DMF). The extent of the peptide couplings was monitored quantitatively by the ninhydrin color test (Kaiser et al., Anal. Biochem. 34, 595-598, 1970). The use of a chaotropic reagent, KSCN, was used to improve active ester mediated coupling wherever necessary. The Boc group was cleaved from the growing peptide chain by treatment with 50% trifluroacetic acid (TFA)/1% anisole in DCM and the liberated N-terminal amine neutralized by a 10% diisopropylethylamine (DIEA) solution in DCM or DMF. After the peptide was assembled on the solid support, it was cleaved from the resin by treatment with anhydrous hydrogen fluoride (HF) and anisole (as the carbonyl scavenger). The crude peptide was extracted by aqueous acetic acid solution or TFA, and purified by preparative High Performance Liquid Chromatography (HPLC). A standard assembly protocol is indicated in Table 2.

TABLE 2

| Operation # | Step # | Operation | No. of Times | Mix Time (mins) |
|---|---|---|---|---|
| I | | Boc-deprotection | | |
| | 1 | Wash DCM | 2 | 2 |
| | 2 | Prewash 50% TFA/DCM (1% anisole) | 1 | 5 |
| | 3 | Deprotect 50% TFA/DCM (1% anisole) | 1 | 20 |
| | 4 | Wash DCM | 3 | 2 |
| | 5 | Wash DCM/DMF::1:1 | 1 | 2 |
| II | | Neutralization | | |
| | 6 | Treat with 10% DIEA/DMF | 2 | 2 |
| | 7 | Wash DCM/DMF::1:1 | 3 | 2 |
| III | | Coupling* | | |
| | 8 | Boc-amino acid (2 eq)/DCM-DMF/HOBt/DIC | 1 | 150-250 |
| | 9 | Wash DCM/DMF::1:1 | 3 | 2 |
| | 10 | Wash DCM | 2 | 2 |

*The efficiency of coupling was monitored using the ninhydrin color reaction, and the % coupling efficiency was calculated from the value of free amine left after the coupling procedure. If the coupling efficiency was determined to be less than 99.5%, a recoupling was performed via a symmetrical anhydride or HOBt/DIC procedure. (HOBt = 1-hydroxybenzotriazole hydrate). If after two couplings the efficiency did not attain 99.5%, a second recoupling was attempted via HOBt/DIC activation in the presence of a chaotropic salt, viz. KSCN, or a capping step with acetic anhydride (Ac2O) and DIEA. For Boc-Gln and Boc-Arg (Tos) the HOBt activated couplings only were used.

EXAMPLE 1

Synthesis of SP-B(53-78)diAcm

A molecule having the sequence (using standard single amino acid code):

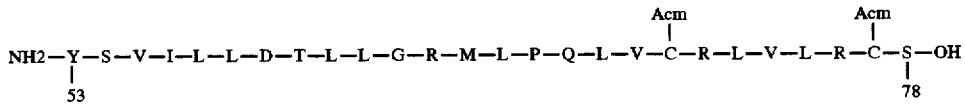

was made so as to provide a replica of the entire 26 amino acid residue sequence of this carboxyl terminal region of the native human SP-B protein. The two cysteine residues, located respectively in positions 71 and 77, were capped with the Acm groups.

This polypeptide was assembled on a Boc-Ser(Bzl)-phenylacetamidomethyl (PAM) resin (Bachem, Calif.) with a substitution ratio of 0.66 meq/gram resin. The general protocol described above was used for the assembly of the protected peptide resin. Boc-amino acids (2 eq) were coupled by HOBt (2 eq) activation mediated by DIC (2.1 eq) in the presence of DCM/DMF (1:1, v/v) as solvent. Trifluoroacetic acid (TFA) in DCM (1:1, v/v) containing anisole was used for deprotection of the Boc-group, followed by neutralization with 10% DIEA/DMF (v/v), and couplings were carried out in DCM/DMF. The extent of coupling was monitored by quantitative ninhydrin analysis.

The functional side chains of various amino acid residues were protected by the following groups:

| | |
|---|---|
| Arg-Tos | (Tosyl) |
| Thr, Ser-Bzl | (Benzyl) |
| Tyr-2-Br-Z | (2-Bromobenzyloxcarbonyl) |
| Cys-Acm | (S-acetamidomethyl) |
| Asp-cHx | (Cyclohexyl). |

Boc-amino acids (standard single letter code) were attached (according to the general protocol outlined supra) to the resin sequentially in the following order: Boc-C(Acm), Boc-R(Tos), Boc-L, Boc-V, Boc-L, Boc-R(Tos), Boc-C (Acm), Boc-V, Boc-L, Boc-Q, Boc-P, Boc-L, Boc-M, Boc-R(Tos), Boc-G, Boc-L, Boc-L, Boc-T(Bzl), Boc-D(cHx), Boc-L, Boc-L, Boc-I, Boc-V, Boc-S(Bzl), Boc-Y(2-Br-Z). This resulted in the generation of the following protected peptide resin:

Y(2-Br-Z)-Ser(Bzl)-V-I-L-L-D(cHx)-T(Bzl)-L-L-G-R(Tos)-M-L-P-Q-L-V-C(Acm)- R (Tos)-L-V-L-R(Tos)-C(Acm)-Ser(Bzl)-Pam Resin.

The protected peptide resin (5.0 gram) was cleaved in the presence of anisole (5 mL) and anhydrous HF (50 mL) at 0° C. for one hour. All HF was removed in vacuo at 0° C. and the peptide resin stirred with 100 mL t-butylmethylether (t-BME) for 5 minutes. The resultant slurry was then filtered, washed with t-BME, and air dried. The peptide was extracted from the dried material by treating with TFA and precipitated from the TFA solution by addition of t-BME (3×30 mL), filtered and air dried.

The resultant crude peptide was purified by reverse phase HPLC using a Vydac C-4 cartridge (5×25 cm). The sample was dissolved in 30% acetic acid/10% acetonitrile and water (100 mL) and purified using a linear 20–60% acetonitrile in water (buffered with 0.1% TFA) solvent elution gradient. Elution time was 100 minutes.

The eluant, at a flow rate of 15–20 mL/min. was monitored at 215 nm. Analytical HPLC (Vydac C-4 column; 0.46×15 cm) was performed to check the purity of the eluted peptide-containing fractions. Pure fractions were combined, concentrated and lyophilized.

Purity of the resultant material was assessed by means of plasma desorption mass spectrometry (PDMS), amino acid composition analysis and HPLC. Amino acid sequence analysis confirmed the correct sequence of the purified material.

EXAMPLE 2

Synthesis of SP-B (53-78)

A molecule having the sequence (using standard single amino acid code):

NH2—Y—S—V—I—L—L—D—T—L—L—G—R—M—L—P—Q—L—V—C—R—L—V—L—R—C—S—OH
|  |
53  78 was made so as to provide a replica of the entire 26 amino acid residue sequence of this carboxyl terminal region of the native human SP-B protein.

The pure SP-B(53-78)diAcm obtained in Example 1 was dissolved in 70% aqueous acetic acid solution (200 mg in 140 mL). A solution of iodine (10 eq) in methanol was then added slowly to the peptide solution. The reaction mixture turned dark brown in color. The oxidation of peptide (disulphide formation between the cysteine residues) was monitored by analytical HPLC, and when complete (1–2 hours at room temperature), the excess iodine was sequenced by adding ascorbic acid until a colorless solution was obtained. The aqueous solution was then concentrated and purified by HPLC on a Vydac C-4 cartridge (5×25 cm). A linear gradient from 20% acetonitrile/80% water (0.1% TFA in water) to 60% acetonitrile/40% water was applied. The eluted fractions were monitored at 215 nm. The desired fractions were combined, concentrated and lyophilized.

Purity of the resultant material was assessed by means of plasma desorption mass spectrometry (PDMS), amino acid composition and HPLC. Amino acid sequence analysis confirmed the correct sequence of the purified material.

EXAMPLE 3

Synthesis of SP-B (58-78)diAla

A molecule having the sequence (using standard single amino acid code):

NH2—L—D—T—L—L—G—R—M—L—P—Q—L—V—A—R—L—V—L—R—A—S—OH
|  |
58  78 was made so as to provide a replica of the entire 21 amino acid residue sequence of this carboxyl terminal region of the native human SP-B protein. The two cysteine residues, located respectively in positions 71 and 77, were each replaced by the amino acid alanine.

This polypeptide was assembled on a Boc-Ser(Bzl)-phenylacetamidomethyl (PAM) resin (Bachem, Calif.) with a substitution ratio of 0.66 meq/gram of resin. The general protocol described above was used for the assembly of the protected peptide resin. Boc-amino acids (2 eq) were coupled by HOBt (2 eq) activation mediated by DIC (2.1 eq) in the presence of DCM/DMF (1:1, v/v) as solvent. Trifluoroacetic acid (TFA) in DCM (1:1, v/v) containing anisole was used for deprotection of the Boc-group, followed by neutralization with 10% DIEA/DMF (v/v), and couplings were carried out in DCM/DMF. The extent of couplings was monitored by quantitative ninhydrin analysis.

The functional side chains of various amino acid residues were protected by the following groups:

| | |
|---|---|
| Arg-Tos | (Tosyl) |
| Thr, Ser-Bzl | (Benzyl) |
| Asp-cHx | (Cyclohexyl) |

The amino acid methionine was used without any side chain protection.

Boc-amino acids (standard single letter code) were attached (according to the general protocol outlined supra) to the resin sequentially in the following order: Boc-S(Bzl), Boc-A, Boc-R(Tos), Boc-L, Boc-V, Boc-L, Boc-R(Tos), Boc-C(Acm), Boc-V, Boc-L, Boc-Q, Boc-P, Boc-L, Boc-M, Boc-R(Tos), Boc-G, Boc-L,Boc-L, Boc-T(Bzl), Boc-D (cHx), Boc-L.

This resulted in the generation of the following protected peptide resin:

L-D(cHx)-T(Bzl)-L-L-G-R(Tos)-M-L-P-Q-L-V-A-R(Tos)-L-V-L-R(Tos)-A-Ser(Bzl)-Pam Resin.

The protected peptide resin (5.0 gram) was cleaved in the presence of anisole (5 mL) and anhydrous HF (50 mL) at 0° C. for one hour. All HF was removed in vacuo at 0° C. and the peptide resin stirred with 100 mL t-butylmethylether (t-BME) for 5 minutes. The resultant slurry was then filtered, washed with t-BME, and air dried. The peptide was extracted from the dried material by treating with TFA and precipitated from the TFA solution by the addition of t-BME (3×30 mL), filtered and air dried.

The resultant crude peptide was purified by reverse phase HPLC using a Vydac C-4 cartridge (5×25 cm). The sample was dissolved in 30% acetic acid/10% acetonitrile and water (100 mL) and purified using a linear 20–60% acetonitrile in water (buffered with 0.1% TFA) solvent elution gradient. Elution time was 100 minutes.

The eluant, at a flow rate of 100–200 mL/min, was monitored at 215 nm. Analytical HPLC (Vydac C-4 column; 0.46×15 cm) was performed to check the purity of the eluted peptide-containing fractions. Pure fractions were combined, concentrated and lyophilized.

Purity of the resultant material was assessed by means of plasma desorption mass spectrometry (PDMS), amino acid composition analysis and HPLC. Amino acid sequence analysis confirmed the correct sequence of the purified material.

Tests were conducted to determine the biophysical (surface) activity of admixtures of phospholipids combined in vitro with each of the purified synthetic peptide fragments either alone or in various fragment combinations.

EXAMPLE 4

Synthetic Peptide Admixture Formulation

Prior to testing for surface activity, the synthetic fragments were admixed with lipids. A lipid mixture consisting of 68% 1,2-dipalmitoyl-sn-phosphatidylcholine (DPPC), 22% egg phosphatidylglycerol (PG) and 9% palmitic acid on a weight basis was prepared by dissolving the lipids in chloroform:methanol (2:1). The required amount of peptide fragment was dissolved in methanol and heated to 60° C. for 10 minutes. The peptide solution was then added to the lipid mixture prewarmed to 45° C. for ten minutes. The samples were mixed at 45° C. by gentle swirling at 100 revolutions per minute on a Buchi rotary evaporator. The organic solvents were then evaporated at 45° C. by increasing the vacuum in 100 torr increments every five minutes until most of the solvent was removed. Final vacuum was between 150–200 torr. Following evaporation, the solids were then suspended in 10% ethanol prewarmed to 45° C. and which was prepared using deionized distilled water. The suspension was gently mixed with vortexing and placed back under vacuum at 600 torr with a repeat of the vacuum ramping process. Final vacuum for the ethanol removal was 50 torr. Following complete removal of ethanol the suspension was diluted with aqueous 0.15M NaCl at 45° C. to yield an admixture with a phospholipid concentration of 25 mg/ml. The peptide/lipid admixtures were formed at final peptide concentrations of 0.5 mg/ml (equivalent to 2% of solids concentration).

Following formulation the admixtures were stored at 4° C. for 48 hours prior to assessment of surface activity by means of biophysical testing.

In order to determine relative surface activity of these admixtures, they were compared to commercially available natural surfactants (Survanta, Abbott Laboratories; Surfacten, Tokyo Tanabe), commercially available synthetic surfactants, (Exosurf, Burroughs-Wellcome) and a lipid admixture standard. This control lipid standard (hereinafter referred to as "Lipid Standard") was prepared as described above but did not contain any peptide material. The commercially available surfactants were utilized as received.

Biophysical testing was assayed using both the modified Wilhelmy balance (Langmuir Trough) system and the pulsating bubble surfactometer (PBS).

For clarity these techniques are briefly described below.

Modified Wilhelmy Surface Balance (a) Surface tension versus compressed surface area.

The dynamic surface tension lowering properties of the peptide/lipid admixtures were studied using a modified Wilhelmy Surface Balance (Langmuir Trough). The instrument consists of an all Teflon trough and movable Teflon ribbon (dam) barrier system which completely contains and defines a variable surface area. Surface area was varied through the use of a constant rate reversible 3-phase motor to drive the Teflon barrier. A Cahn 2000 electrobalance (Cahn Instruments, Cerittos, Calif.) with a sandblasted 1 cm platinum plate and stainless steel hangdown wire was employed to determine the surface tension at the liquid-air interface. The entire apparatus was situated in a thermostated incubator set at 45° C. Surface area-surface tension measurements were made by adding 950 ml of 0.15M NaCl to the trough. Subphase temperature was controlled during the measurements at 36°–38° C.

For each experiment 27 ul of peptide/lipid admixture was applied in a random array of 13 droplets to the surface of the temperature controlled subphase and allowed to spread spontaneously for 3 minutes. (The 27 ul application corresponds to 675 ug of phospholipid). The trough surface area was then cycled from a maximum (445 sq. cm) to a minimum (178 sq. cm) surface area and back to maximum at a cycling rate of 3 cycles/min (compression ratio 2.5:1). The dynamic surface tension versus surface area was recorded for 7 complete compression-expansion cycles for each application.

(b) Absorption Rate

A procedure similar to that described by Notter, et al., Pediatric Res. 16, 515–519 (1982) was employed to determine the absorption rate in the absence of diffusion resistance. The modified Wilhelmy surface balance as described above was used. However, instead of using a Langmuir trough, a round Teflon dish (5.1 cm diameter) was employed. The subphase, 70 ml of 0.15M NaCl, was allowed to equilibrate to 37° C. in the incubator and was continuously stirred with a Teflon coated magnetic stirrer. An aliquot of the peptide/lipid fragment admixture containing 5 mg of total phospholipid was dispersed in 10 ml of 0.15M NaCl by vortexing for 10 seconds. This dispersion was then added to the saline subphase. Surface tension lowering was monitored using a strip chart recorder connected to the electro-balance output.

Details of these techniques are as described in Notter, et al., Pediatric Res. 16, 515–519 (1982); Notter et al., Chem Phys. Lipids 33, 67–80 (1983); Egan et al., J. Applied Physiol. 55, 875–883 (1983); Bermel et al., Lung 162, 99–113 (1984); Notter, et al., Pediatric Res. 20, 569–577 (1985); Hole, et al., Chem Phys Lipids 38, 287–298 (1985).

The Pulsating Bubble Surfactometer (PBS)

The PBS equipment (Electronetics, Buffalo, N.Y.) used was essentially equivalent to that described in detail by G. Enhorning, J. Appld. Physiol. 43, 198–203, (1977). Recordings were made of the pressure gradient across the wall of a small air bubble, communicating with ambient air by means of a narrow chimney stack, but otherwise entirely surrounded by a 40 ul volume of the peptide/lipid admixture. The admixture concentration employed for these studies was 1 mg/ml total phospholipid (0.02 mg/ml total peptide) and the diluent was 0.15M NaCl.

Immediately prior to loading the sample chamber, the diluted samples were sonicated for 15 seconds to remove any gas nuclei.

The pressure drop across the air-water interface was measured during pulsation by a pressure transducer, and the corresponding surface tension was determined at minimum and maximum bubble size through the application of Young's law and the Laplace equation. Measurements were all made at 37° C. and the bubble pulsed at 20 cycles/minute to render respectively a maximum (1.1 mm) and a minimum (0.8 mm) bubble diameter. (This compression/expansion corresponds to a 50% change in the surface area of the air-water interface).

Dynamic surface tension and absorption facility are summarized in Tables 3 and 4 below. Table 3 summarizes the dynamic surface tension and adsorption data obtained with the various peptide-lipid admixtures on the Wilhelmy Balance -Langmuir Trough System. To one skilled in the art, it is obvious using this experimental setup that low minimum dynamic surface tension values (less than 10 dynes/cm) and reduced adsorption surface tension values (less than 50 dynes/cm) are desirable properties of a good surfactant formulation. Low maximum surface tension values (less than 60 dynes/cm) are also desirable.

TABLE 3

Dynamic Surface Tension and Adsorption Capacity of Synthetic Peptide Fragment Admixtures as determined by the Modified Wilhelmy Balance-Langmuir Trough System.

| Sample | | Surface Tension[a] (dynes/cm) Maximum | Minimum | Adsorption[b] (dynes/cm) |
|---|---|---|---|---|
| (a) | Controls | | | |
| | Survanta | 39.0 | 7.5 | 33.5 |
| | Surfacten | 51.5 | 2.5 | 26.0 |
| | Exosurf (No protein) | 63.0 | 12.0 | 58.0 |
| | Lipid Standard (No protein) | 61.0 | 16.0 | 60.0 |
| | SP-B(1–78) | 44.0 | 0.3 | 37.5 |

TABLE 3-continued

Dynamic Surface Tension and Adsorption Capacity of Synthetic Peptide Fragment Admixtures as determined by the Modified Wilhelmy Balance-Langmuir Trough System.

| Sample | | Surface Tension[a] (dynes/cm) Maximum | Minimum | Adsorption[b] (dynes/cm) |
|---|---|---|---|---|
| (b). | Peptide Fragments | | | |
| | SP-B(53–70) | 49.0 | 1.2 | 44.0 |
| | SP-B(53–78) | 50.4 | 1.1 | 47.0 |
| | SP-B(53–78)diAcm | 49.5 | 0.1 | 47.0 |
| | SP-B(58–70) | 64.5 | 4.4 | 46.0 |
| | SP-B(58–70)diAla | 57.0 | 0.2 | 39.7 |
| | SP-B(58–78)diAcm | 55.0 | 1.0 | 43.5 |
| | SP-B(63–70) | 68.5 | 15.4 | 61.0 |
| | SP-B(63–78)diAla | 50.5 | 2.2 | 45.5 |
| | SP-B(63–78)diAcm | 52.0 | 1.3 | 44.0 |
| | SP-B(66–78) | 50.7 | 0.7 | 47.5 |
| | SP-B(66–78)diAcm | 55.6 | 1.6 | 47.0 |
| | SP-B(66–78)diLys | 56.5 | 2.6 | 48.9 |
| | SP-B(66–78)diAla | 53.5 | 1.0 | 44.0 |
| | SP-B(69–78) | 65.0 | 6.3 | 56.5 |
| | SP-B(69–78)diAla | 66.0 | 12.7 | 50.0 |
| | SP-B(69–78)diAcm | 65.6 | 5.7 | 51.7 |

[a]Minimum/Maximum values recorded during seven complete cycles. In all cases 675 ug of phospholipid was added to the Langmuir Trough at maximum dimensions of 445 sq. cm.
[b]Equilibrium adsorption measured after three (3) minutes spreading time.
[c]Tanaka Lipids: DPPC:PG:PA::68:22:9.
[d]Peptide concentration is 0.5 mg/ml (~2% of solids).

From the data contained in Table 3 above, it is clear that most of the synthetic SP-B Fragment admixtures significantly reduces the minimum dynamic surface tension to an extent that is comparable or better than that exhibited by natural surfactant (e.g. Survanta). With two exceptions only, all of the Peptide Fragment Admixtures yield a dynamic minimum surface tension value of less than 10 dyne/cm whereas natural surfactant (e.g. Survanta) yields a minimum dynamic surface tension of about 8 dynes/cm.

Table 4 summarizes the surface tension values at the air-aqueous interface obtained for the various peptide-admixtures on the pulsating bubble surfactometer. As with the Wilhelmy Balance, to one skilled in the art it will be obvious that admixtures which result in the generation low surface tension values at minimum bubble size are typically classified as effective surfactant compositions. Minimum surface tension values less than 10 mN/m2 are deemed desirable.

TABLE 4

Surface tension values obtained at minimum and maximum bubble size using the Pulsating Bubble Surfactometer. Values given are determined after 5 minutes pulsation (100 cycles). (Values in parenthesis are standard deviations).

| Sample[a] | | Surface tension[b] (dyne/cm) Minimum | Maximum |
|---|---|---|---|
| (a). | Controls | | |
| | Survanta | 4.6 (0.4) | 55.9 (1.2) |
| | Surfacten | 4.7 (0.2) | — |
| | Exosurf | 29.8 (0.1) | 57.8 (0.7) |
| | Tanaka Lipids (No protein) | 23.5 (0.1) | 66.7 (0.7) |
| | SP-B(1–78) | 4.7 (0.3) | 50.6 (1.7) |

TABLE 4-continued

Surface tension values obtained at minimum and maximum bubble size using the Pulsating Bubble Surfactometer. Values given are determined after 5 minutes pulsation (100 cycles). (Values in parenthesis are standard deviations).

| Sample[a] | Surface tension[b] (dyne/cm) | |
|---|---|---|
| | Minimum | Maximum |
| (b). Peptide Fragment c | | |
| SP-B(53–70) | 11.2 (0.7) | 51.7 (2.5) |
| SP-B(53–78) | 1.5 (0.6) | 56.7 (2.9) |
| SP-B(53–78)diAcm | 4.1 (3.1) | 54.1 (2.6) |
| SP-B(58–70) | 7.2 (2.0) | 58.5 (2.4) |
| SP-B(58–78)diAla | 7.5 (1.2) | 52.0 (3.3) |
| SP-B(58–78)diAcm | 8.2 (0.9) | 55.0 (2.4) |
| SP-B(63–70) | 22.0 (0.7) | 65.3 (1.3) |
| SP-B(63–78)diAla | 5.3 (2.9) | 48.0 (3.4) |
| SP-B(63–78)diAcm | 1.7 (1.8) | 51.4 (6.7) |
| SP-B(66–78) | 9.4 (1.4) | 61.5 (5.4) |
| SP-B(66–78)diAcm | 1.6 (0.1) | 58.8 (1.6) |
| SP-B(66–78)diLys | 1.8 (0.5) | 55.1 (6.6) |
| SP-B(66–78)diAla | 6.0 (1.0) | 53.0 (1.3) |
| SP-B(69–78) | 27.3 (0.5) | 64.0 (5.0) |
| SP-B(69–78)diAla | 8.9 (0.3) | 60.9 (0.9) |
| SP-B(69–78)diAcm | 15.2 (1.3) | 65.5 (2.4) |

[a]All samples run at a concentration of 1 mg/ml phospholipid; diluent employed was 0.15M NaCl in glass distilled deionized water; temperature = 37° C., and a pulsation cycle of 20 cycles/minute.
[b]Values reported are those obtained after 5 minute pulsation time, i.e. after 100 pulsations, at maximum and minimum bubble radius.
[c]Total peptide concentration in all cases is 2% of phospholipids (0.5 mg/ml).

It is clear from the data contained in Table 4 that many of the SP-B fragments examined significantly enhances the surface tension lowering capacity of the carrier lipids. However, as with the data shown in Table 3, there are clearly different levels of surface activity associated with the different peptide fragments.

The data contained in both Tables 3 and 4, as evidenced by the minimum surface tension values, demonstrates that certain admixtures of phospholipid and peptide fragments of this invention exhibit markedly improved surface activity as compared to admixtures containing synthetic lipids only and are comparable to the two commercial formulations Survanta and Surfacten.

EXAMPLE 5

Relative Surface Activity of SP-B Peptide Fragments

As shown in Tables 3 and 4, most of the peptide fragments shown in Table 1 are able to lower significantly the minimum surface tension of the carrier lipids. Thus in order to determine which of the various fragments exhibited superior activity and to define further the relative surface activity of the various peptide fragments (admixed with the standard lipid mixture described in Example 4), the peptide concentration of 0.5 mg/ml (2% of solids) was reduced in order to establish (on the modified Wilhelmy surface balance) the lowest peptide concentration which exhibited surface activity. For the purpose of this comparison "surface activity" is defined as follows: For any given peptide concentration, the admixture is required to result in a minimum dynamic surface tension of less than 10 dynes/cm for each of seven consecutive expansion/compression cycles.

Initially each of the admixtures was formulated so as to contain an equal number of moles of the individual peptide as is contained in a 0.5 mg/mL admixture of SP-B(53–78).

This enabled the assessment of individual peptide surface activity relative to a comparable number of SP-B(53–78) molecules contained in the same lipid admixture. Thereafter, each of these admixtures was diluted with the standard lipid mixture as described in Example 4, so as to provide doubling dilutions of the equimolar "parent" stock peptide admixture. The lipid concentration in all cases was maintained at 25 mg/ml.

Assessment of relative surface activity was conducted on the modified Wilhemy-Langmuir Surface Balance. For these studies a standard volume of 27 ul of each admixture, corresponding to a total phospholipid mass of 675 ug, was applied to the Langmuir Trough with maximum dimensions of 445 sq. cm. The results of this study are shown below in Table 5.

For the purpose of interpreting the data contained in Table 5, it should be recognized that the more effective (i.e. surface active) SP-B fragments will meet the designated criteria at lower peptide concentrations (higher dilution factor), i.e. the lower the peptide concentration that is required in order to meet the designated surface activity criterion, the more surface active is that peptide fragment. Table 5 does not list data for the lipid control since no protein (peptide) is contained therein.

TABLE 5

Relative Surface Activity of Single Peptide Admixtures as determined by dilution studies performed on the modified Wilhelmy Balance-Langmuir Trough.

| | Mean Minimum Surface Tension (mN/m2) Determined Using the Wilhelmy Surface Balance as a Function of Relative Peptide (Protein) Concentration | | | | | |
|---|---|---|---|---|---|---|
| Samples | 2% | Equimolar | ½ | ¼ | ⅛ | ⅟₁₆ |
| SP-B(1–78) | 1.6 | 1.5 | 1.5 | 4.5 | 21.5 | n.d. |
| SP-B(53–70) | 1.2 | 0.9 | 5.6 | 19.7 | 18.7 | 19.5 |
| SP-B(53–78) | 0.1 | 0.7 | 0.6 | 0.5 | 2.0 | 14.5 |
| SP-B(53–78)diAcm | 0.1 | n.d. | n.d. | n.d. | n.d. | n.d. |
| SP-B(58–70) | 4.4 | 10.5 | 13.5 | 14.0 | 16.2 | n.d. |
| SP-B(58–78)diAla | 0.2 | 0.0 | 0.3 | 1.5 | 4.7 | 24.1 |
| SP-B(58–78)diAcm | 1.0 | 1.2 | 1.7 | 3.2 | 4.0 | 16.0 |
| SP-B(63–70) | 13.7 | n.d. | n.d. | n.d. | n.d. | n.d. |
| SP-B(63–78)diAla | 2.2 | 1.9 | 2.5 | 2.5 | 3.0 | 7.9 |
| SP-B(63–78)diAcm | 1.3 | 1.3 | 1.0 | 10.5 | 14.4 | 20.6 |
| SP-B(66–78) | 0.7 | 0.6 | 2.8 | 6.7 | 14.9 | 22.0 |
| SP-B(66–78)diAcm | 1.0 | 2.4 | 2.6 | 4.3 | 19.0 | n.d. |
| SP-B(66–78)diLys | 2.6 | 2.5 | 8.2 | 7.0 | 15.0 | 23.0 |
| SP-B(66–78)diAla | 1.0 | 1.5 | 1.0 | 0.9 | 2.3 | 22.4 |
| SP-B(69–78) | 6.3 | 13.3 | 12.5 | 13.8 | 12.2 | n.d. |
| SP-B(69–78)diAla | 10.7 | n.d. | n.d. | n.d. | n.d. | n.d. |
| SP-B(69–78)diAcm | 5.7 | 9.5 | 9.0 | 12.8 | 13.1 | 13.5 |

[a]In all cases 675 ug phospholipid was applied to the Langmuir Trough at maximum expansion (445 sq. cm). Subphase was 0.15M NaCl in glass distilled deionized water. Phospholipid concentration was maintained at 25 mg/ml in all cases.
[b]n.d. = not done. Testing was not continued when the samples exhibited a minimum surface tension greater than 10 mN/m2.

The data contained in Table 5 clearly demonstrates that the various peptide fragments exhibit varying and different degrees of surface activity as determined by these dilution studies.

It is clear from the data contained in Tables 3, 4 and 5 that the SP-B peptide fragments according to this invention, produce markedly enhanced surface activity as compared to synthetic lipids alone or synthetic lipids plus other peptide fragments. However, as shown in Table 5, the different peptide fragments clearly exhibit different levels of surface activity. The unusual surface activity exhibited by particularly by the following peptides SP-B(53–78)diAcm, SP-B (58-78)diAcm, SP-B(58-78)diAla, SP-B(63-78)diAla and SP-B(66-78)diAla is both surprising and unexpected and, forms in part, the basis for the present invention.

Industrial Applicability

This invention overcomes numerous problems associated with natural, synthetic or recombinant SP-B (1-78). It is quite apparent that production of only portions of the Carboxyl terminal region of the SP-B (1-78) molecule will enhance and accelerate the commercial production of pulmonary surfactant products.

The foregoing detailed description is given for clearness of understanding only, and no unnecessary limitation should be understood therefrom, as modifications will be obvious to those skilled in the art.

We claim:

1. A composition of matter comprising at least one fragment of the SP-B protein that exhibits surfactant activity when admixed with at least one phospholipid, wherein said fragment:

(a) has no cysteine residues capable of forming intra- or intermolecular polymerization by disulfide linkage; and (b) is selected from the group consisting of:

$$\underset{58}{NH2\text{-}L}\text{-D-T-L-L-G-R-M-L-P-Q-}\underset{70}{L\text{-V-OH}} \quad (ii)$$

$$\underset{58}{NH2\text{-}L}\text{-D-T-L-L-G-R-M-L-P-Q-L-V-C-R-L-V-L-R-}\underset{78}{\overset{Acm}{|}}\text{-S-OH} \quad (iii)$$

$$\underset{58}{NH2\text{-}L}\text{-D-T-L-L-G-R-M-L-P-Q-L-V-A-R-L-V-L-R-A-}\underset{78}{S}\text{-OH} \quad (iv)$$

$$\underset{63}{NH2\text{-}G}\text{-R-M-L-P-Q-}\underset{70}{L\text{-V-OH}} \quad (v)$$

$$\underset{63}{NH2\text{-}G}\text{-R-M-L-P-Q-L-V-}\overset{Acm}{\underset{|}{C}}\text{-R-L-V-L-R-}\overset{Acm}{\underset{|}{C}}\text{-S-OH} \quad (vi)$$

$$\underset{63}{NH2\text{-}G}\text{-R-M-L-P-Q-L-V-A-R-L-V-L-R-A-}\underset{78}{S}\text{-OH} \quad (vii)$$

$$\underset{66}{NH2\text{-}L}\text{-P-Q-L-V-}\overset{Acm}{\underset{|}{C}}\text{-R-L-V-L-R-}\overset{Acm}{\underset{|}{C}}\text{-S-OH} \quad (viii)$$

$$\underset{66}{NH2\text{-}L}\text{-P-Q-L-V-A-R-L-V-L-R-A-}\underset{78}{S}\text{-OH} \quad (ix)$$

$$\underset{66}{NH2\text{-}L}\text{-P-Q-L-V-K-R-L-V-L-R-K-}\underset{78}{S}\text{-OH} \quad (x)$$

$$\underset{69}{NH2\text{-}L}\text{-V-}\overset{Acm}{\underset{|}{C}}\text{-R-L-V-L-R-}\overset{Acm}{\underset{|}{C}}\text{-S-OH} \text{ and} \quad (xi)$$

$$\underset{69}{NH2\text{-}L}\text{-V-A-R-L-V-L-R-A-}\underset{78}{S}\text{-OH.} \quad (xii)$$

2. A composition of matter according to claim 1 and further comprising at least one lipid.

3. A composition of matter according to claim 2 wherein the lipid is selected from the group consisting of synthetic phospholipids, naturally occurring phospholipids, neutral lipids, cholesterol, cholesteryl esters, phosphatidylcholine, disaturated phosphatidylycholine, phosphatidylglycerol, dipalmitoyl phosphatidylcholine, phosphatidylinisotyl and mixtures thereof.

4. A composition of matter according to claim 2 wherein the composition is characterized by the amino acid sequence:

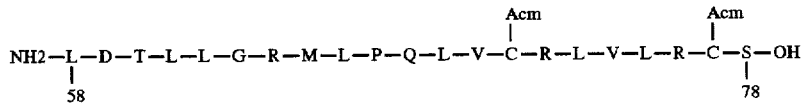

5. A composition of matter according to claim 2 wherein the composition is characterized by the amino acid sequence:

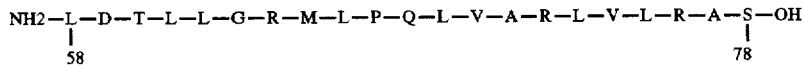

6. A composition of matter according to claim 2 wherein the composition is characterized by the amino acid sequence:

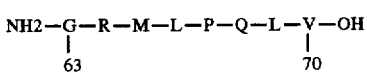

7. A composition of matter according to claim 2 wherein the composition is characterized by the amino acid sequence:

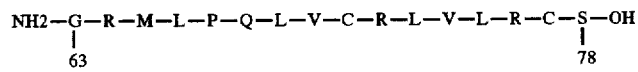

8. A composition of matter according to claim 2 wherein the composition is characterized by the amino acid sequence:

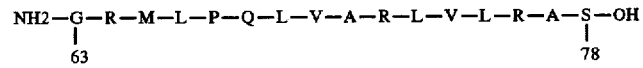

9. A composition of matter according to claim 2 wherein the composition is characterized by the amino acid sequence:

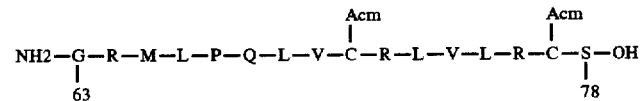

10. A composition of matter according to claim 2 wherein the composition is characterized by the amino acid sequence:

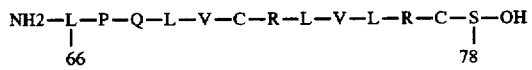

11. A composition of matter according to claim 2 wherein the composition is characterized by the amino acid sequence:

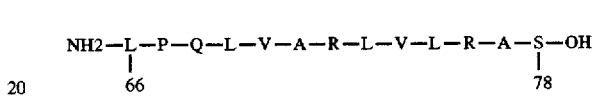

12. A composition matter according to claim 2 wherein the composition is characterized by the amino acid sequence:

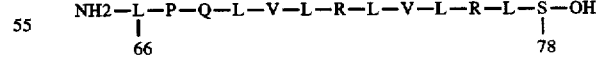

13. A composition of matter according to claim 2 wherein the composition is characterized by the amino acid sequence:

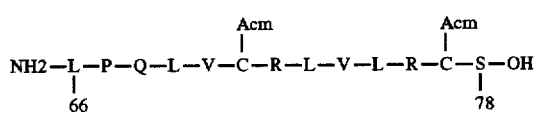

14. A composition of matter according to claim 2 wherein the composition is characterized by the amino acid sequence:

NH2—L—V—C—R—L—V—L—R—C—S—OH
       |                    |
       69                   78

15. A composition of matter according to claim 2 wherein the composition is characterized by the amino acid sequence:

NH2—L—V—A—R—L—V—L—R—A—S—OH
       |                    |
       69                   78

16. A composition of matter according to claim 2 wherein the composition is characterized by the amino acid sequence:

```
              Acm              Acm
               |                |
NH2—L—V—C—R—L—V—L—R—C—S—OH
       |                    |
       69                   78
```

17. A composition of matter comprising at least one peptide fragment from carboxy terminal 26 residues of the SP-B protein, wherein said peptide fragment is characterized in that:

(a) it exhibits surfactant activity when admixed with at least one phospholipid;

(b) it comprises from 10 to 26 amino acid residues; and (c) in it active form, contains no cysteine residues capable of forming intra- or intermolecular polymerization by disulfide linkage, thereby rendering said fragment monomeric.

18. The composition of matter of claim 17, further comprising a phospholipid.

19. The composition of matter of claim 17, wherein said peptide fragment consists of an amino acid sequence in a region of said SP-B protein, which region is devoid of cysteine residues.

20. The composition of matter of claim 17 wherein all cysteine residues present in said fragment are blocked from oxidation and polymerization by a covalently bound Acm group.

21. The composition of matter of claim 17 wherein said fragment contains an amino acid residue other than cysteine as a replacement for any cysteine residues present in the native SP-B protein in the region of said fragment.

22. The composition of matter of claim 21, wherein said residue other than cysteine is Alanine or Lysine.

23. The composition of matter of claim 17 wherein said peptide fragment is selected from the group consisting of:

NH2-L-D-T-L-L-G-R-M-L-P-Q-L-V-OH (ii)
    |                        |
    58                       70

```
                                  Acm           Acm              (iii)
                                   |             |
NH2-L-D-T-L-L-G-R-M-L-P-Q-L-V-C-R-L-V-L-R-C-S-OH
    |                                          |
    58                                         78
```

NH2-L-D-T-L-L-G-R-M-L-P-Q-L-V-A-R-L-V-L-R-A-S-OH (iv)
    |                                          |
    58                                         78

NH2-G-R-M-L-P-Q-L-V-OH (v)
    |             |
    63            70

```
           Acm           Acm                    (vi).
            |             |
NH2-G-R-M-L-P-Q-L-V-C-R-L-V-L-R-C-S-OH
    |                              |
    63                             78
```

NH2-G-R-M-L-P-Q-L-V-A-R-L-V-L-R-A-S-OH (vii)
    |                              |
    63                             78

```
           Acm           Acm          (viii)
            |             |
NH2-L-P-Q-L-V-C-R-L-V-L-R-C-S-OH
    |                        |
    66                       78
```

NH2-L-P-Q-L-V-A-R-L-V-L-R-A-S-OH (ix)
    |                        |
    66                       78

NH2-L-P-Q-L-V-K-R-L-V-L-R-K-S-OH (x)
    |                        |
    66                       78

```
          Acm           Acm           (xi)
           |             |
NH2-L-V-C-R-L-V-L-R-C-S-OH  and
    |                    |
    69                   78
```

NH2-L-V-A-R-L-V-L-R-A-S-OH. (xii)
    |                    |
    69                   78

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 18 amino acid residues
    ( B ) TYPE: amino acid
    ( C ) STRANDEDNESS: single
    ( D ) TOPOLOGY: linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:SP-B(53-70)
    ( B ) LOCATION:
    ( C ) IDENTIFICATION METHOD:
    ( D ) OTHER INFORMATION: Surfactant polypeptide;
        Fragment 53- 70 of surfactant-active protein
        known as SP- B, SAP-B, SAP-(Phe), SAP-6 (Phe)
        or SPL- (Phe)

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:1:

Tyr Ser Val Ile Leu Leu Asp Thr Leu Leu Gly Arg Met Leu Pro
              5                  10                 15

Gln Leu Val ( 2 ) INFORMATION FOR SEQ ID NO:2:

( i ) SEQUENCE CHARACTERISTICS:
        ( A ) LENGTH: 26 amino acid residues
        ( B ) TYPE: amino acid
        ( C ) STRANDEDNESS: single
        ( D ) TOPOLOGY:linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:SP-B(53-78)
        ( B ) LOCATION:
        ( C ) IDENTIFICATION METHOD:
        ( D ) OTHER INFORMATION: Surfactant polypeptide;
            Fragment 53- 78 of surfactant-active protein
            known as SP- B, SAP-B, SAP-(Phe), SAP-6 (Phe)
            or SPL- (Phe)

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:2:

Tyr Ser Val Ile Leu Leu Asp Thr Leu Leu Gly Arg Met Leu Pro
            5                        10                    15

Gln Leu Val Cys Arg Leu Val Leu Arg Cys Ser
               20                     25

( 2 ) INFORMATION FOR SEQ ID NO:3:

( i ) SEQUENCE CHARACTERISTICS:
        ( A ) LENGTH: 26 amino acid residues
        ( B ) TYPE: amino acid
        ( C ) STRANDEDNESS: single
        ( D ) TOPOLOGY:linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:SP-B(53-78)diAcm
    ( B ) LOCATION:
    ( C ) IDENTIFICATION METHOD:
    ( D ) OTHER INFORMATION: Surfactant polypeptide;
        Fragment 53- 78 of surfactant-active protein
        known as SP- B, SAP-B, SAP-(Phe), SAP-6 (Phe)
        or SPL- (Phe); modified at positions 71 and 77
        by providing each of the cysteine residues at
        these positions with an S-acetamidomethyl (Acm)
        group.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:3:

Tyr Ser Val Ile Leu Leu Asp Thr Leu Leu Gly Arg Met Leu Pro
            5                          10                      15

Gln Leu Val Xaa Arg Leu Val Leu Arg Xaa Ser
            20                      25

( 2 ) INFORMATION FOR SEQ ID NO:4:

( i ) SEQUENCE CHARACTERISTICS:
    ( A ) LENGTH: 13 amino acid residues
    ( B ) TYPE: amino acid
    ( C ) STRANDEDNESS: single
    ( D ) TOPOLOGY: linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
    ( A ) ORGANISM:
    ( B ) STRAIN:

( C ) INDIVIDUAL ISOLATE:
              ( D ) DEVELOPMENTAL STAGE:
              ( E ) HAPLOTYPE:
              ( F ) TISSUE TYPE:
              ( G ) CELL TYPE:
              ( H ) CELL LINE:
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
              ( A ) NAME/KEY:SP-B(58-70)
              ( B ) LOCATION:
              ( C ) IDENTIFICATION METHOD:
              ( D ) OTHER INFORMATION: Surfactant polypeptide;
                    Fragment 58- 70 of surfactant-active protein
                    known as SP- B, SAP-B, SAP-(Phe), SAP-6 (Phe)
                    or SPL- (Phe)

( x ) PUBLICATION INFORMATION:
              ( A ) AUTHORS:
              ( B ) TITLE:
              ( C ) JOURNAL:
              ( D ) VOLUME:
              ( E ) ISSUE:
              ( F ) PAGES:
              ( G ) DATE:
              ( H ) DOCUMENT NUMBER:
              ( I ) FILING DATE:
              ( J ) PUBLICATION DATE:
              ( K ) RELEVANT RESIDUES IN SEQ ID NO:

( x i ) SEQUENCE DESCRIPTION: SEQ ID NO:4:

Leu Asp Thr Leu Leu Gly Arg Met Leu Pro Gln Leu Val
                  5                   10

( 2 ) INFORMATION FOR SEQ ID NO:5:

( i ) SEQUENCE CHARACTERISTICS:
              ( A ) LENGTH: 21 amino acid residues
              ( B ) TYPE: amino acid
              ( C ) STRANDEDNESS: single
              ( D ) TOPOLOGY:linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
              ( A ) ORGANISM:
              ( B ) STRAIN:
              ( C ) INDIVIDUAL ISOLATE:
              ( D ) DEVELOPMENTAL STAGE:
              ( E ) HAPLOTYPE:
              ( F ) TISSUE TYPE:
              ( G ) CELL TYPE:
              ( H ) CELL LINE:
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
    ( A ) NAME/KEY:SP-B(58-78)diAla
    ( B ) LOCATION:
    ( C ) IDENTIFICATION METHOD:
    ( D ) OTHER INFORMATION: Surfactant polypeptide;
        Fragment 58- 78 of surfactant-active protein known
        as SP-B, SAP- B, SAP-(Phe), SAP-6 (Phe) or SPL-(Phe);
        modified at positions 71 and 77 by replacing each of
        the cysteine residues at these positions with an
        alanine residue.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:5:

Leu Asp Thr Leu Leu Gly Arg Met Leu Pro Gln Leu Val Ala Arg
             5                    10              15

Leu Val Leu Arg Ala Ser
          20

( 2 ) INFORMATION FOR SEQ ID NO:6:

( i ) SEQUENCE CHARACTERISTICS:
        ( A ) LENGTH: 21 amino acid residues
        ( B ) TYPE: amino acid
        ( C ) STRANDEDNESS: single
        ( D ) TOPOLOGY:linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: SP-B(58-78)diAcm
        ( B ) LOCATION:
        ( C ) IDENTIFICATION METHOD:
        ( D ) OTHER INFORMATION: Surfactant polypeptide;
            Fragment 58- 78 of surfactant-active protein known
            as SP-B, SAP- B, SAP-(Phe), SAP-6 (Phe) or SPL-(Phe);
            modified at positions 71 and 77 by providing each of
            the cysteine residues at these positions with an
            S- acetamidomethyl (Acm) group.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:6:

```
Leu Asp Thr Leu Leu Gly Arg Met Leu Pro Gln Leu Val Xaa Arg
              5                   10                  15
Leu Val Leu Arg Xaa Ser
              20
```

( 2 ) INFORMATION FOR SEQ ID NO:7:

( i ) SEQUENCE CHARACTERISTICS:
    ( A ) LENGTH: 8 amino acid residues
    ( B ) TYPE: amino acid
    ( C ) STRANDEDNESS: single
    ( D ) TOPOLOGY: linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY: SP-B(63-70)
    ( B ) LOCATION:
    ( C ) IDENTIFICATION METHOD:
    ( D ) OTHER INFORMATION: Surfactant polypeptide;
        Fragment 63- 70 of surfactant-active protein
        known as SP- B, SAP-B, SAP-(Phe), SAP-6 (Phe)
        or SPL- (Phe)

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:7:

Gly Arg Met Leu Pro Gln Leu Val
                  5

( 2 ) INFORMATION FOR SEQ ID NO:8:

( i ) SEQUENCE CHARACTERISTICS:
        ( A ) LENGTH: 16 amino acid residues
        ( B ) TYPE: amino acid
        ( C ) STRANDEDNESS: single
        ( D ) TOPOLOGY:linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:SP-B(63-78)diAla
        ( B ) LOCATION:
        ( C ) IDENTIFICATION METHOD:
        ( D ) OTHER INFORMATION: Surfactant polypeptide;
        Fragment 63- 78 of surfactant-active protein known
        as SP-B, SAP- B, SAP-(Phe), SAP-6 (Phe) or SPL-(Phe);
        modified at positions 71 and 77 by replacing each of
        the cysteine residues at these positions with an
        alanine residue.

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:8:

Gly Arg Met Leu Pro Gln Leu Val Ala Arg Leu Val Leu Arg Ala
                  5                   10                  15

Ser ( 2 ) INFORMATION FOR SEQ ID NO:9:

( i ) SEQUENCE CHARACTERISTICS:
        ( A ) LENGTH: 16 amino acid residues
        ( B ) TYPE: amino acid (C) STRANDEDNESS: single
(D) TOPOLOGY: linear (ii) MOLECULE TYPE: polypeptide (iii) HYPOTHETICAL: no (iv) ANTI-SENSE:

(v) FRAGMENT TYPE:

(vi) ORIGINAL SOURCE:
 (A) ORGANISM:
 (B) STRAIN:
 (C) INDIVIDUAL ISOLATE:
 (D) DEVELOPMENTAL STAGE:
 (E) HAPLOTYPE:
 (F) TISSUE TYPE:
 (G) CELL TYPE:
 (H) CELL LINE:
 (I) ORGANELLE:

(vii) IMMEDIATE SOURCE:
 (A) LIBRARY:
 (B) CLONE:

(viii) POSITION IN GENOME:
 (A) CHROMOSOME/SEGMENT:
 (B) MAP POSITION:
 (C) UNITS:

(ix) FEATURE:
 (A) NAME/KEY:SP-B(63-78)diAcm
 (B) LOCATION:
 (C) IDENTIFICATION METHOD:
 (D) OTHER INFORMATION: Surfactant polypeptide;
  Fragment 63- 78 of surfactant-active protein
  known as SP- B, SAP-B, SAP-(Phe), SAP-6 (Phe)
  or SPL- (Phe); modified at positions 71 and 77
  by providing each of the cysteine residues at
  these positions with an S-acetamidomethyl (Acm)
  group.

(x) PUBLICATION INFORMATION:
 (A) AUTHORS:
 (B) TITLE:
 (C) JOURNAL:
 (D) VOLUME:
 (E) ISSUE:
 (F) PAGES:
 (G) DATE:
 (H) DOCUMENT NUMBER:
 (I) FILING DATE:
 (J) PUBLICATION DATE:
 (K) RELEVANT RESIDUES IN SEQ ID NO:

(xi) SEQUENCE DESCRIPTION: SEQ ID NO:9:

Gly Arg Met Leu Pro Gln Leu Val Xaa Arg Leu Val Leu Arg Xaa
                  5                   10                  15
Ser (2) INFORMATION FOR SEQ ID NO:10:

(i) SEQUENCE CHARACTERISTICS:
 (A) LENGTH: 13 amino acid residues
 (B) TYPE: amino acid
 (C) STRANDEDNESS: single
 (D) TOPOLOGY: linear (ii) MOLECULE TYPE: polypeptide (iii) HYPOTHETICAL: no (iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:SP-B(66-78)
    (B) LOCATION:
    (C) IDENTIFICATION METHOD:
    (D) OTHER INFORMATION: Surfactant polypeptide;
        Fragment 66- 78 of surfactant-active protein
        known as SP- B, SAP-B, SAP-(Phe), SAP-6 (Phe)
        or SPL- (Phe)

(x) PUBLICATION INFORMATION:
    (A) AUTHORS:
    (B) TITLE:
    (C) JOURNAL:
    (D) VOLUME:
    (E) ISSUE:
    (F) PAGES:
  (A) CHROMOSOME/SEGMENT:
(B) MAP POSITION:
(C) UNITS:

(ix) FEATURE:
(A) NAME/KEY: SP-B(66-78)diLys
(B) LOCATION:
(C) IDENTIFICATION METHOD:
(D) OTHER INFORMATION: Surfactant polypeptide; Fragment 66- 78 of surfactant-active protein known as SP- B, SAP-B, SAP-(Phe), SAP-6 (Phe) or SPL- (Phe); modified at positions 71 and 77 by replacing each of the cysteine residues at these positions with a lysine residue.

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:11:

Leu Pro Gln Leu Val Lys Arg Leu Val Leu Arg Lys Ser
                  5                   10

(2) INFORMATION FOR SEQ ID NO:12:

(i) SEQUENCE CHARACTERISTICS:
(A) LENGTH: 13 amino acid residues
(B) TYPE: amino acid
(C) STRANDEDNESS: single
(D) TOPOLOGY: linear (ii) MOLECULE TYPE: polypeptide (iii) HYPOTHETICAL: no (iv) ANTI-SENSE:

(v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:SP-B(66-78)diAla
(B) LOCATION:
(C) IDENTIFICATION METHOD:
(D) OTHER INFORMATION: Surfactant polypeptide; Fragment 66- 78 of surfactant-active protein known as SP- B, SAP-B, SAP-(Phe), SAP-6 (Phe) or SPL- (Phe); modified at positions 71 and 78 by replacing each of the cysteine residues at these positions with an alanine residue.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:12:

Leu Pro Gln Leu Val Ala Arg Leu Val Leu Arg Ala Ser
                5                        10

( 2 ) INFORMATION FOR SEQ ID NO:13:

( i ) SEQUENCE CHARACTERISTICS:
        ( A ) LENGTH: 13 amino acid residues
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: SP-B(66-78)diAcm
        ( B ) LOCATION:
        ( C ) IDENTIFICATION METHOD:
        ( D ) OTHER INFORMATION: Surfactant polypeptide;
            Fragment 66- 78 of surfactant-active protein known
            as SP-B, SAP- B, SAP-(Phe), SAP-6 (Phe) or SPL-(Phe);
            modified at positions 71 and 77 by providing each
            of the cysteine residues at these positions with
            an S- acetamidomethyl (Acm) group.

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:13:

Leu Pro Gln Leu Val Xaa Arg Leu Val Leu Arg Xaa Ser
                      5                   10

( 2 ) INFORMATION FOR SEQ ID NO:14:

( i ) SEQUENCE CHARACTERISTICS:
        ( A ) LENGTH: 10 amino acid residues
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:SP-B(69-78)
        ( B ) LOCATION:
        ( C ) IDENTIFICATION METHOD:
        ( D ) OTHER INFORMATION: Surfactant polypeptide;
            Fragment 69- 78 of surfactant-active protein
            known as SP- B, SAP-B, SAP-(Phe), SAP-6 (Phe) or
            SPL- (Phe)

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:14:

Leu Val Cys Arg Leu Val Leu Arg Cys Ser
                  5                   10

( 2 ) INFORMATION FOR SEQ ID NO:15:

( i ) SEQUENCE CHARACTERISTICS:
        ( A ) LENGTH: 10 amino acid residues
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY: SP-B(69-78)diAla
                ( B ) LOCATION:
                ( C ) IDENTIFICATION METHOD:
                ( D ) OTHER INFORMATION: Surfactant polypeptide;
                        Fragment 69- 78 of surfactant-active protein
                        known as SP- B, SAP-B, SAP-(Phe), SAP-6 (Phe)
                        or SPL- (Phe); modified at positions 71 and 78
                        by replacing each of the cysteine residues at
                        these positions with an alanine residue.

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:15:

Leu Val Ala Arg Leu Val Leu Arg Ala Ser
            5                   10

( 2 ) INFORMATION FOR SEQ ID NO:16:

( i ) SEQUENCE CHARACTERISTICS:
                ( A ) LENGTH: 10 amino acid residues
                ( B ) TYPE: amino acid
                ( C ) STRANDEDNESS: single
                ( D ) TOPOLOGY: linear ( i i ) MOLECULE TYPE: polypeptide ( i i i ) HYPOTHETICAL: no ( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:

(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: SP-B(69-78)diAla
(B) LOCATION:
(C) IDENTIFICATION METHOD:
(D) OTHER INFORMATION: Surfactant polypeptide;
Fragment 69- 78 of surfactant-active protein
known as SP- B, SAP-B, SAP-(Phe), SAP-6 (Phe)
or SPL- (Phe); modified at positions 71 and 77
by providing each of the cysteine residues at
these positions with an S-acetamidomethyl (Acm)
group.

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:16:

Leu Val Xaa Arg Leu Val Leu Arg Xaa Ser
              5                       10

(2) INFORMATION FOR SEQ ID NO:17:

(i) SEQUENCE CHARACTERISTICS:
(A) LENGTH: 16 amino acid residues
(B) TYPE: amino acid
(C) STRANDEDNESS: single
(D) TOPOLOGY:linear (ii) MOLECULE TYPE: polypeptide (iii) HYPOTHETICAL: no (iv) ANTI-SENSE:

(v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:

(A) NAME/KEY: SP-B(63-78)
(B) LOCATION:
(C) IDENTIFICATION METHOD:
(D) OTHER INFORMATION: Surfactant polypeptide;
    Fragment 63-78 of surfactant-active protein
    known as SP-B, SAP-B, SAP-(Phe), SAP-6 (Phe)
    or SPL- (Phe)

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:17:

Gly Arg Met Leu Pro Gln Leu Val Cys Arg Leu Val Leu Arg Cys
              5                   10                      15
Ser